United States Patent [19]

Strebelle

[11] Patent Number: 5,059,730
[45] Date of Patent: Oct. 22, 1991

[54] PROCESS FOR THE PURIFICATION OF VINYL CHLORIDE

[75] Inventor: Michel Strebelle, Brussels, Belgium

[73] Assignee: Solvay & Cie (Société Anonyme), Brussels, Belgium

[21] Appl. No.: 531,343

[22] Filed: May 31, 1990

[30] Foreign Application Priority Data

Jun. 2, 1989 [FR] France .................. 89 08234

[51] Int. Cl.$^5$ ............................. C07C 17/38
[52] U.S. Cl. .................................. 570/238
[58] Field of Search ............................ 570/238

[56] References Cited

U.S. PATENT DOCUMENTS 2,356,562  8/1944  Beig et al. .
2,816,148  12/1957  Anderson et al. .................. 570/238

FOREIGN PATENT DOCUMENTS 1406502  9/1975  United Kingdom .

Primary Examiner—Howard T. Mars
Attorney, Agent, or Firm—Spencer & Frank

[57] ABSTRACT

Process for the removal from vinyl chloride of compounds of the ester type by an operation of treatment comprising an alkaline washing and a treatment with a bisulphite.

5 Claims, 1 Drawing Sheet

PROCESS FOR THE PURIFICATION OF VINYL CHLORIDE

FIELD OF THE INVENTION

The present invention relates to a process for the removal from vinyl chloride of compounds of the ester type and more particularly from ester compounds containing an unsaturation in the molecule, such as vinyl acetate.

BACKGROUND TECHNOLOGY

It is known that the vinyl chloride employed in industry is a compound which can be obtained according to various methods of manufacture which have been optimized so as to produce a compound whose purity is high and, in all cases, sufficient for the uses for which this compound is usually intended and most particularly for its homopolymerization.

A completely different problem which has recently arisen in industry, for economic and environmental reasons, is the problem presented by the purification of residual vinyl chloride, unconverted or originating from industrial processes in which it has been used. In this context the problem presented by the separation of vinyl chloride from esters such as vinyl acetate occupies a special place, since it relates to the separation of two comonomers resulting from a copolymerization operation in which, for lack of a satisfactory solution in respect of the recycling of the two comonomers, it was accepted to lose all or some of the two monomers using nonselective destructive operations such as burning.

SUMMARY OF THE INVENTION

A new process has now been found which does not have the abovementioned disadvantages and which, by destroying the ester compound, enables very pure vinyl chloride to be recovered, and this makes it possible to employ it for an application identical with that of a vinyl chloride originating directly from a monomer production unit.

To this end, the present invention relates to a process for the removal from vinyl chloride of compounds of the ester type exhibiting an enol ester structure, characterized in that the vinyl chloride undergoes a treatment comprising an alkaline washing stage followed by a stage of treatment with a bisulphite.

DETAILED DESCRIPTION OF THE INVENTION

Figure 1:
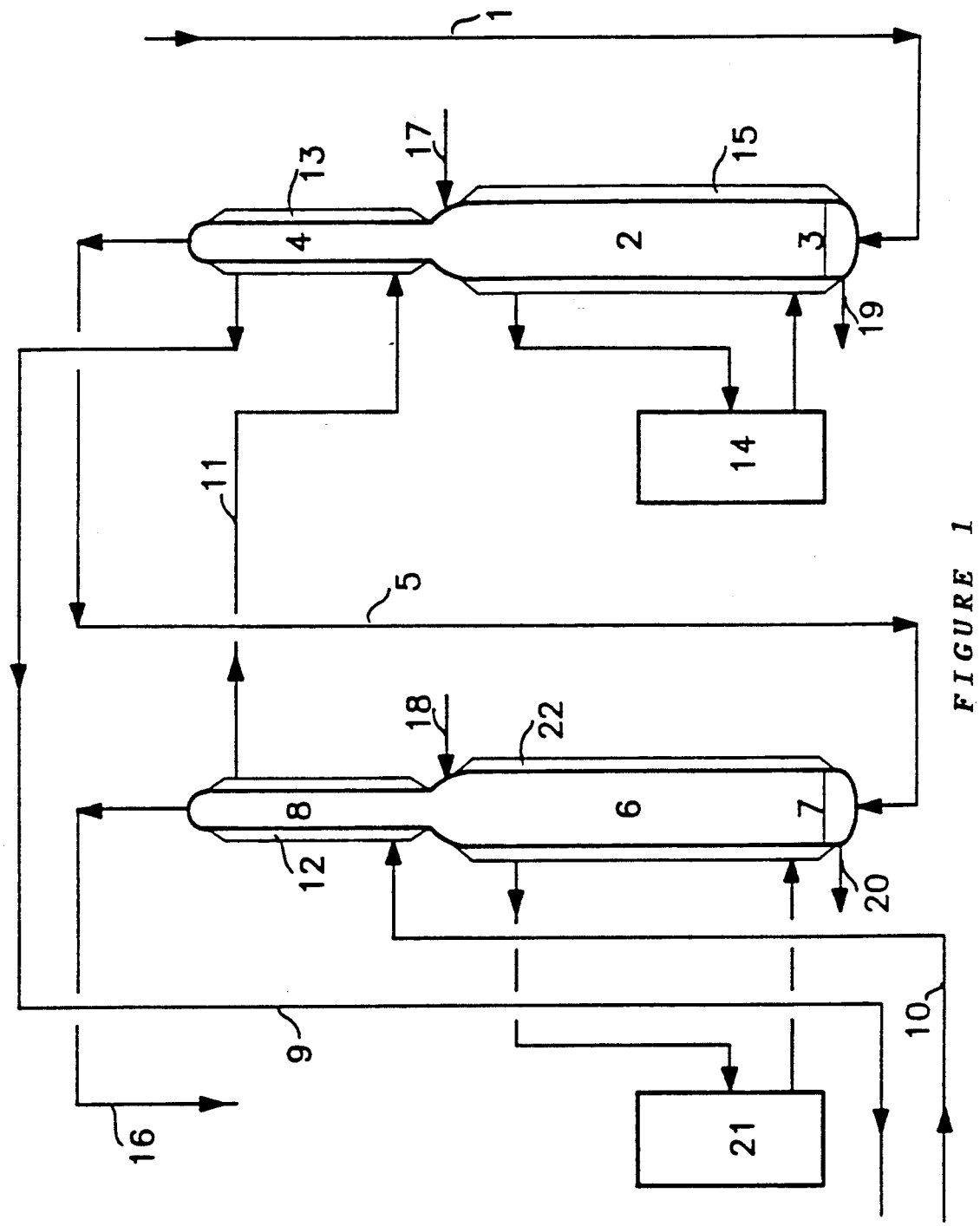
FIG. 1 is a diagram of a plant carrying out the process of the invention.

The present invention relates to a process for the removal from vinyl chloride of compounds of the ester type exhibiting an enol ester structure, wherein the vinyl chloride undergoes a treatment comprising an alkaline washing stage followed by a stage of treatment with a bisulfite.

The ester-type compounds exhibiting an enol ester structure, which are generally present in vinyl chloride are compounds capable of copolymerizing with vinyl chloride by a radical route. On hydrolysis, these compounds, of the enol ester type give ketonic or aldehyde carbonyl derivatives capable of forming addition compounds with a bisulphite, either aldehydes in general or methyl ketones and cyclic ketones. A compound of this kind which has produced good results is vinyl acetate. It is obvious, however, that the process of the invention is readily applied to any type of unsaturated ester exhibiting an enol ester structure which may be found in vinyl chloride for any reasons whatever.

The stage of alkaline washing of the impure vinyl chloride can in principle be carried out with any known basic agent, but is usually carried out with an aqueous solution of a base derived from alkali or alkaline-earth metals. This treatment is preferably carried out with a hydroxide of these metals. Finally, good results have been obtained with sodium hydroxide. Although the present invention is not intended to be limited in any way or to be subject to any scientific explanation or theory, it is highly probable that the alkaline treatment converts all the ester compound to a salt and an aldehyde. Thus, more particularly in the case of vinyl acetate, sodium acetate and acetaldehyde would appear to be formed at this stage when the process is performed using sodium hydroxide.

When the alkaline washing stage is carried out with an aqueous solution of sodium hydroxide, the NaOH concentration is generally between 0.01 M/l and 10 M/l and preferably between 0.1 M/l and 2 M/l.

The alkaline washing stage is followed by a stage of treatment of the vinyl chloride with a bisulphite, and this has the result of purifying the vinyl chloride probably by removing aldehydes, such as the residual acetaldehyde, present in the mixture. Among the bisulphites, the operation is generally carried out with alkali metal bisulphites; good results have been observed with sodium bisulphite.

The bisulphites of the invention may be obtained by any known process such as the addition of water to metabisulphite or the addition of acid to sulphites.

When the treatment is carried out with sodium bisulphite, the operation is advantageously carried out at a pH which is controlled and, in all cases, lying between the values of 5 and 9 in order to avoid the formation of excessively large quantities of $SO_2$ in the reaction mixture. The pH of the mixture will be preferably maintained between the values included between 6.5 and 8.5.

The pH control may be ensured by any means allowing this effect to be achieved. A means which has given good results consists in adding sodium sulphite in sufficient quantities to attain the desired pH.

When the treatment is carried out with an aqueous solution of sodium bisulphite, the $NaHSO_3$ concentration is generally between 0.01 M/l and the solubility limit of this compound in water in the temperature and pressure conditions in question. However, the concentration is preferably between 0.05 and 1 M/l.

The bisulphite treatment may be carried out using an aqueous solution containing only the bisulphite or may be carried out in the presence of other components which do not affect the proper progress of the reaction. Thus, an embodiment which has given good results consists in combining the operation of drying the vinyl chloride with that of the bisulphite treatment. To do this, the operation is preferably carried out with mixtures of NaCl and $NaHSO_3$ whose freezing point is sufficiently low to ensure the removal of the acetaldehyde and simultaneously the drying of the vinyl chloride. During such an operation the treatment is advantageously performed in a drying scrubber maintained in the region of $-10°$ C.

Apart from the abovementioned stages, whose operational sequence is essential for obtaining ester-free vinyl chloride, the process of the invention may provide other stages according to the particular conditions which have led to such a vinyl chloride.

When carried out using sodium bisulphite on vinyl chloride originating from a manufacture of copolymerization of vinyl chloride and vinyl acetate, the process of the invention can be carried out in temperature conditions which are usually between −20° C. and 50° C. and preferably between 0° and 10° C. insofar as the alkaline washing stage is concerned and between −15° and 40° C. and preferably between −10° and 35° C. insofar as the bisulphite stage is concerned.

With regard to the pressure conditions, these are not critical and are usually between 1 and 10 bars in the case of both stages. The two stages are usually performed at atmospheric pressure.

The process of the invention can be carried out in any plant allowing the stages described above to be performed and comprising immersed, sprayed or packed columns capable of operating either batchwise or continuously. A diagram of a plant which has given good results is reproduced in FIG. 1 and comprises:

a conduit 1 by which gaseous vinyl chloride containing the ester to be removed is introduced into the system, a first reactor 2, equipped with a jacket 15, into which the impure vinyl chloride is introduced via the conduit 1. This reactor 2 is advantageously equipped with a device for distributing gases into the liquid 3 and with a condenser 4 permitting good bubbling of the gases to be carried out and the liquid products to be retained at the alkaline washing temperature respectively, a conduit 5 connecting the condenser 4 of the reactor 2 to a second reactor 6 intended for carrying out the bisulphite treatment, this reactor 6 is again advantageously equipped with a device for distributing gases into the liquid 7 and with a condenser 8 whose functions are identical with those of the device 3 and of the condenser 4, the pure vinyl chloride is then conveyed by the conduit 16 to the drying followed by a recompression and a liquefaction in order to permit the storage of pure vinyl chloride, finally, the plant is completed by a refrigeration circuit enabling, via the conduits 10 and 11, the condensers 4 and 8 to be cooled using the jackets 12 and 13 and, using independent refrigeration circuits 14 and 21, enabling the cooling of the jacket 15 of the alkaline washing reactor 2 and of the jacket 22 of the reactor 6 to be ensured respectively.

In addition, the reactors 2 and 6 may be equipped for functioning continuously or noncontinuously. To this end, conduits 17 and 18 are provided in order to feed them with aqueous solutions NaOH and of bisulphite respectively. Furthermore, in order to keep the level constant in the reactors 2 and 6, the latter also comprise "purge" conduits 19 and 20, which enable the partially exhausted aqueous solutions to be removed.

The plant may be made wholly or partially of any suitable material, coated or otherwise with polymeric compounds which make it possible to improve the resistance of the materials to some of the reactants used. The whole plant is usually made of stainless steel.

The vinyl chloride recovered at the outlet of the second reactor can be employed in any manufacture and more particularly for the manufacture of high-purity homopolymers.

Lastly, although the invention relates to the removal from vinyl chloride of compounds of ester type exhibiting an enol ester structure, it is obvious that it can also be suitable, without other fundamental modification, for the purification of other monomers of the same type, such as vinylidene chloride, vinyl fluoride and vinylidene fluoride, as well as the removal from these compounds of some ketonic or aldehyde impurities capable of reacting with the bisulphite and whose origin is not the enol ester.

The invention is illustrated by the following examples.

EXAMPLE 1

The operation is carried out in a plant such as illustrated in FIG. 1, in which the column 2 and the column 6 have a diameter of 65 mm, a height of 550 mm and a liquid capacity of 400 cm$^3$.

Column 2, kept at a temperature of 6° C. by cooling, contains a 2-molar aqueous solution of NaOH and the composition at the bottom of column 6, kept at 25° C., consists of a 0.1 M aqueous solution of NaHSO$_3$.

Vinyl chloride recovered from a plant for copolymerization with vinyl acetate, containing 2,500 ppm by vol. of vinyl acetate is introduced into this plant via the conduit 1 at a gas flow rate of approximately 145 Nl/h (i.e. normal liters measured at 0° C. and at atmospheric pressure/hour) during a total test period of 6 h.

The following results were observed:

| NaHSO$_3$ reactor entry: | |
|---|---|
| Vinyl acetate in ppm by vol. | <1 |
| Acetaldehyde in ppm by vol. | 250 |
| NaHSO$_3$ reactor exit: | |
| Vinyl acetate in ppm by vol. | <1 |
| Acetaldehyde in ppm by vol. | <1 |
| SO$_2$ in ppm by vol. | 60 |

In the light of the above results it may be concluded that the process of the invention makes it possible to remove quantitatively all the vinyl acetate present in the vinyl chloride and that the latter consequently has a purity enabling it to be recycled. It may also be concluded from these results that, when the bisulphite treatment is performed without pH control, measurable quantities of SO$_2$ are formed.

EXAMPLE 2

The operation is carried out in conditions identical with those of Example 1 but with the pH being controlled by introducing NaSO$_3$ in a quantity such that the pH stays at a value of 5.5 throughout the experiment.

In these conditions the results observed are the same as in Example 1 with the exception of the SO$_2$ result alone, which falls to 3.5 ppm by vol.

EXAMPLE 3

The operation is carried out in the conditions of Example 1, but introducing enough NaSO$_3$ to make it possible to work at a pH of 8 throughout the experiment and it is observed that, in these conditions, the quantity of SO$_2$ formed is lower than 0.1 ppm by vol., all other results being maintained.

From the examples it may therefore be concluded that the process of the invention, performed without any special precaution (Example 1), enables all the vinyl acetate to be destroyed and that, when this process is performed with pH control (Examples 2 and 3), it makes it possible to minimize or even to avoid any $SO_2$ formation.

I claim:

1. Process for the removal from vinyl chloride of compounds of the unsaturated ester type exhibiting an enol ester structure, characterized in that the impure vinyl chloride undergoes a treatment comprising an alkaline washing stage followed by a stage of treatment with an alkali metal bisulphite.

2. Process according to claim 1, characterized in that the alkaline washing stage is carried out with an aqueous solution of a base derived from alkali or alkaline-earth metals.

3. Process according to claim 1, characterized in that the bisulphite used is sodium bisulphite.

4. Process according to claim 3, characterized in that the alkaline washing stage is followed by a stage of treatment with sodium bisulphite with control of the pH between values included between, 6.5 and 8.5.

5. Process according to claim 1, characterized in that the ester present in the impure vinyl chloride is vinyl acetate.

* * * * *